Figure 1:
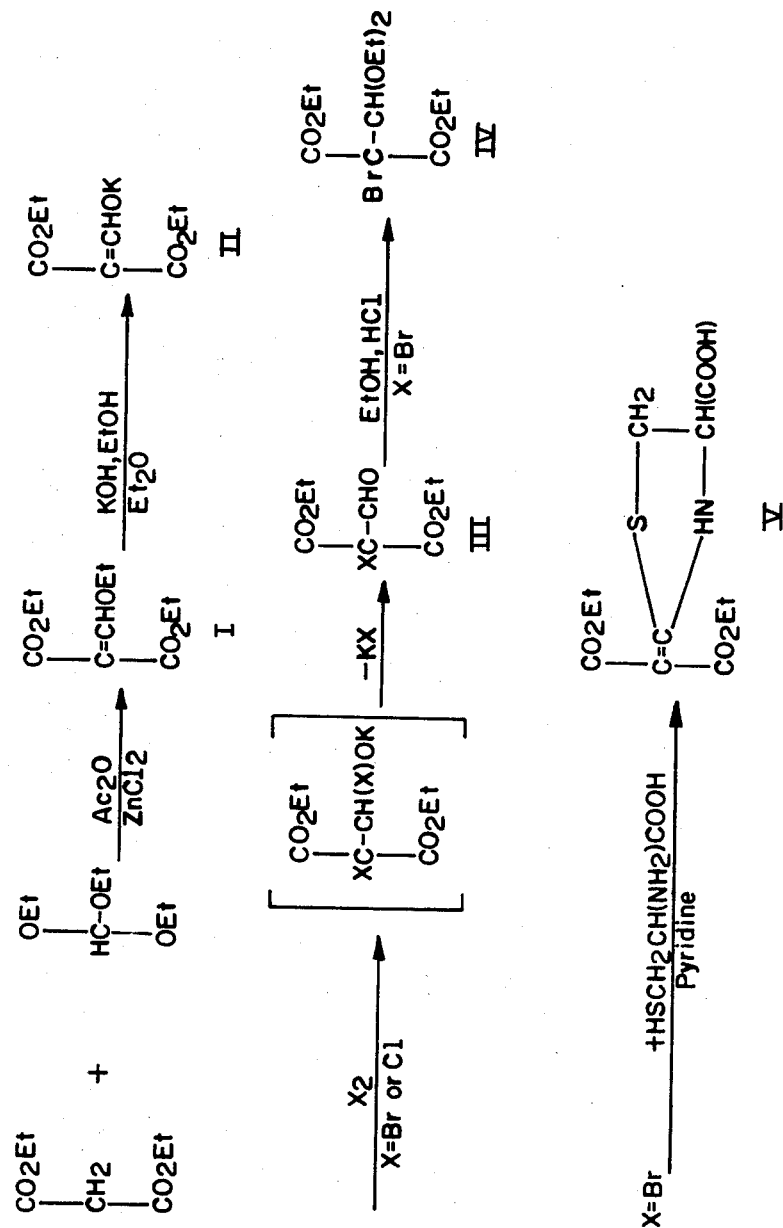

United States Patent [19]
Wolff

[11] Patent Number: 4,600,781
[45] Date of Patent: Jul. 15, 1986

[54] 2-FORMYL-2-HALOMALONATES AND COMPOUND DERIVED THEREFROM

[75] Inventor: Ivan A. Wolff, Oreland, Pa.

[73] Assignee: The United States of America as represented by the Secretary of Agriculture, Washington, D.C.

[21] Appl. No.: 626,960

[22] Filed: Jul. 2, 1984

[51] Int. Cl.$^4$ .................. C07D 277/14; C07C 69/67; C07C 67/307
[52] U.S. Cl. .................. 548/201; 560/176; 560/180
[58] Field of Search ............... 560/176, 180; 568/484; 548/201

[56] References Cited

U.S. PATENT DOCUMENTS 3,239,570  3/1966  Slaugh et al. .................. 560/176
4,172,208  10/1979  Crutchfield et al. ............... 560/176

FOREIGN PATENT DOCUMENTS 0180458  10/1983  Japan .................. 560/176
7001927  8/1970  Netherlands .................. 548/201

OTHER PUBLICATIONS

C. F. Allen, J.A.C.S., vol. 52, (1930), pp. 2955–2959.
P. Z. Bedoukian, J.A.C.S., vol. 66, (1944), pp. 651–652 and 1325–1327.
R. A. Swaringen, Jr. et al., *J. Org. Chem.*, vol. 44, No. 26, (1979), pp. 4825–4829.
I. A. Wolff et al., *Chem. Abs.* 102:112847u, (1985).

*Primary Examiner*—Natalie Trousof
*Assistant Examiner*—L. Hendriksen
*Attorney, Agent, or Firm*—M. Howard Silverstein; William E. Scott; David G. McConnell

[57] ABSTRACT

The invention relates to 2-formyl-2-halomalonates, and their preparation. The compounds are useful in the preparation of their acetals and also in the preparation of 2-(dicarbethoxymethylene)thiazolidine-4-carboxylic acid.

5 Claims, 1 Drawing Figure

2-FORMYL-2-HALOMALONATES AND COMPOUND DERIVED THEREFROM

BACKGROUND OF THE INVENTION

Field of the Invention

This invention relates to the preparation of some new malonic ester derivatives and to the derivatives themselves.

Description of the Art

A diethyl acetal prepared by the process of this invention was previously synthesized by the reaction of alpha-bromo diethyl malonate with triethyl orthoformate (J. Org. Chem. 44, 4825, 1979). However, the presence of the compound was assessed by NMR assay and was not separated from the other products of the reaction. Other references that may be of interest are, JACS 66, 651, 1325, 1944 and JACS 52, 2955, 1930.

SUMMARY OF THE INVENTION

An object of this invention is to provide some new malonic ester derivatives.

Another object of this invention is to provide a method of preparing the new malonic ester derivatives.

According to this invention, the above objects are accomplished by halogenating the potassium salt of oxymethylene diethyl malonate to prepare 2-halogen-2-formyl malonic esters. Reaction of the 2-bromo-2-formyl malonic ester with ethanol in the presence of HCl produces the diethyl acetal, while reaction with cysteine produces the thiazolidine.

DESCRIPTION OF THE INVENTION

Malonic ester derivatives are widely used synthetic intermediates especially in the pharmaceutical industry. The diethyl acetal noted above to have been previously synthesized was reported to have utility for making medicinally important substances (J. Org. Chem. 44, 4825-4829, 1979).

The compounds synthesized and reactions reported are summarized in the schematic of FIG. 1.

The preparation of ethoxymethylene diethyl malonate I and of the potassium salt II have been previously reported (Org. Syn., Coll. Vol. 3, 395, 1955; Ann. 297, 76, 1897). When dry II, suspended in carbon tetrachloride was halogenated at 0° C., 65–70 percent yields of the 2-halogen-2-formyl malonic esters III were obtained. In FIG. 1, the reaction is shown for illustration only as addition of a molecule of halogen followed by loss of KX.

The properties of the bromo aldehyde III (X=Br), which has been more thoroughly investigated than the chloro compound, are unusual. The compound gives a positive fuchsin aldehyde test, and readily provides a 2,4-dinitrophenylhydrazone. No oxime, semicarbazone, or bisulfite addition product was obtained by usual procedures. The aldehyde is labile to alkali. Titration of an alcoholic solution indicates an alkali uptake of 0.5–0.6 milliequivalent per millimole of aldehyde.

The bromine in neither the aldehyde nor its acetal is removed by boiling alcoholic silver nitrate solution. Also, the bromoaldehyde liberates iodine from acidified potassium iodide solution, a typical reaction of "positive" or "oxidizing" halogen atoms.

The aldehyde III (X=Br) is readily converted to its diethyl acetal, the compound synthesized as noted above, by the reaction of alpha-bromo diethyl malonate with triethyl orthoformate.

Reaction of III (X=Br) with cysteine gave thiazolidine V. The thiazolidine structure V was indicated by (a) the close qualitative and quantitative agreement of its absorption spectrum with those of compounds containing similar types of conjugated systems, and (b) the isolation of diethyl oxomalonate as a product of oxidation of the compound by potassium permanganate. The oxidizing nature of the bromine atom in diethyl 2-formyl2-bromomalonate III is further illustrated by the consistent production of substantial quantities of cystine, in addition to the thiazolidine V, when III was reacted with l-cysteine.

Diethyl 2-formyl-2-chloromalonate III (X=Cl) does not react readily with l-cysteine to form a thiazolidine under the experimental conditions used for the bromo compound.

The physical constants and analytical results for the compounds are shown in Table I.

The invention will now be exemplified with more particularity.

Potassium oxymethylene diethyl malonate, II 225 g of pure ethoxymethylene diethyl malonate I was dissolved in 2,700 ml of dry ether in a 5-liter three-necked flask equipped with a stirrer, a thermometer which extended into the liquid, and a dropping funnel. The mixture was cooled to 0° C. and one equivalent of approximately 1 N KOH in absolute ethanol was added dropwise with stirring over the period of 30–60 minutes The solution turned light yellow. Within about 15 minutes precipitation of the K salt began. The temperature was maintained at ±1° C. After about an hour the flask contained a yellow mush. After approximately two more hours the K salt was separated by filtration and dried in vacuo. The yield of crude salt was 213 g. This was recrystallized from absolute ethanol. The purified potassium oxymethylene diethyl malonate had m.p. 240° C. II reacted with acetyl chloride in dry diethyl ether, first in the cold and then under reflux for 2 hours gave diethyl acetoxymethylene malonate, b.p. 106°–110° C./0.6 torr, $d_{25}{}^{25}=1.133$, $n_D{}^{25}=1.4521$, U.V. (95% EtOH)$\lambda_{max}=227.5$ nm., $E_{1\ cm}{}^{1\%}=660$.

Diethyl 2-formyl-2-bromomalonate III (X=Br)

71.7 g (0.318 mole) of pure powdered potassium oxymethylene diethyl malonate II was suspended in 150 ml of dry carbon tetrachloride. To the cooled suspension was added, over the period of about an hour, with intermittent shaking, a solution of 50.9 g of bromine (0.318 mole) in 100 ml of carbon tetrachloride. The mixture was then allowed to stand at room temperature for one hour. The potassium bromide was separated by filtration, and the carbon tetrachloride solution was concentrated in vacuo in a stream of nitrogen. There was 69.0 g of crude aldehyde (81 percent of the theoretical yield). This was fractionally distilled in vacuo in a stream of nitrogen. 56.1 g of product distilled at 81°–85° C./0.5 torr (66 percent of the theoretical yield). The major cut had $d_{24}{}^{24}=1.430$ and $n_D{}^{25}=1.4581$, U.V.(95% ethanol)$\lambda_{max}=247.5$ nm., $E_{1\ cm.}{}^{1\%}=62.1$. Diethyl 2-formyl-2-bromomalonate is sensitive to alkali and to oxidation by air. The fractions should be placed under nitrogen as soon as distilled and stored out of contact with the air.

Diethyl 2-formyl-2-bromomalonate, III (X=Br) gave a 90 percent yield of 2,4-dinitrophenylhydrazone, m.p.

Diethyl 2-formyl-2-bromomalonate diethyl acetal, IV 83.3 g of diethyl 2-formyl-2-bromomalonate was dissolved in 350 ml of 6.3 N HCl in absolute ethanol which had previously been cooled in an ice bath. The mixture was kept cool for an hour and then allowed to stand at room temperature overnight. The alcoholic HCl was removed in vacuo (nitrogen), an additional quantity of dry ethanol added, and the solution concentrated again. The residue was then exactly neutralized (pH test paper) with NaOEt in absolute ethanol and filtered. The salt was washed with small portions of absolute ethanol. The acetal was fractionally distilled in vacuo. The yield of acetal that distilled at 114°–115° C./0.5 torr was 31 percent of the theoretical. The distilled acetal had $n_D^{25} = 1.4533$ and $d_{24}^{24} = 1.274$.

Diethyl 2-formyl-2-chloromalonate III (X=Cl)

Fifteen g of recrystallized potassium oxymethylene diethyl malonate II was suspended in 100 ml of carbon tetrachloride. The mixture was cooled in an ice bath, and dry chlorine gas was passed in until a weight increase of 4.7 g was obtained. This required approximately two hours. The solid potassium salt went into solution and a gelatinous precipitate settled out. After the mixture stood for two hours longer at room temperature, the precipitate was separated by filtration, the carbon tetrachloride was distilled from the filtrate in vacuo, and the liquid residue was then fractionated in vacuo at 0.8 torr. The total yield of distilled aldehyde was 10.4 g, or 69 per cent of the theoretical amount. The major portion distilled at 80°–82° C./0.8 torr. It had $d_{25}^{25} = 1.202$, and $n_D^{25}$ 1.4348.

l-2-(dicarbethoxymethylene)-thiazolidine-4-carboxylic acid, V

To 11.0 g of l-cysteine hydrochloride monohydrate in 25 ml of water was added 16.8 g of diethyl 2-formyl-2-bromomalonate in 35 ml of absolute ethanol. The reaction mixture became warm. After the mixture stood overnight under nitrogen 6.1 g of pyridine was added whereupon an immediate precipitation of l-cystine (2.1 g) occurred. This was filtered after several hours. The filtrate was made alkaline with an excess of saturated sodium bicarbonate solution, extracted several times with chloroform, and then acidified to pH of 2. The product precipitated as a gummy solid which soon flocculated on standing. The yield of this crude material melting at 157°–160° C. was 4.0 g (22 percent of the theoretical). Occasionally the crude thiazolidine contained cystine. This was easily removed by recrystallization from methanol in which cystine is insoluble. The thiazolidine can be recrystallized from methanol, ethanol, or 50 percent ethanol. Recrystallized V had a m.p. of 158°–160° C., U.V. (abs. ethanol) $\lambda_{max.} = 280$ nm., $E_{1cm.}^{1\%} = 700$.

Oxidation of l-2-(dicarbethoxymethylene)-thiazolidine-4-carboxylic acid

To 1 g of the thiazolidine dissolved in 100 ml of glacial acetic acid was added dropwise with stirring a solution containing 3 g of potassium permanganate in 75 ml of water. Slight warming of the reaction mixture was noted. The permanganate was decolorized rapidly. Stirring was continued for four hours at room temperature. The solution was then allowed to stand overnight, was filtered and decolorized with gaseous sulfur dioxide. Water was added and the mixture was continuously extracted for several hours with ether. Evaporation of the ether and acetic acid in vacuo left a partially crystalline material which was used directly for the preparation of hydrazone derivatives. When a strongly acidified ($H_2SO_4$) aqueous alcoholic solution of 2,4-dinitrophenylhydrazine was added to the residue, about 150 mg of the 2,4-dinitrophenylhydrazone of diethyl oxomalonate was isolated; it melted at 115°–117° C. after one recrystallization from ethanol. The residue also reacted rapidly with p-tolylhydrazine in dilute acetic acid solution to give a hydrazone melting at 140°–142° C. (recrystallized from light petroleum ether). This was the monoethyl ester of the p-tolyhydrazone of oxomalonic acid. This oxidation was carried out to obtain structural information.

TABLE I

| Compound | Molecular Formula | m.p. or b.p. °C. | Analytical values Calc. | Found |
|---|---|---|---|---|
| II | $C_8H_{11}O_5K$ | m.p. ca. 267° | K = 17.3 | 17.4 |
| III, X = Br | $C_8H_{11}O_5Br$ | b.p. 82°/0.5 torr | C = 36.0 | 36.1 |
|  |  |  | H = 4.15 | 4.24 |
| III, X = Br 2,4-dinitrophenylhydrazone | $C_{14}H_{15}BrN_4O_8$ | m.p. 133–135° | N = 12.5 | 12.6 |
|  |  |  | Br = 17.9 | 17.5 |
|  |  |  | OEt = 20.2 | 20.3 |
| III, X = Cl | $C_8H_{11}O_5Cl$ | b.p. 80–82°/0.8 torr | C = 43.2 | 42.8 |
|  |  |  | H = 4.94 | 5.21 |
| III, X = Cl 2,4-dinitrophenylhydrazone | $C_{14}H_{15}ClN_4O_8$ | m.p. 128–129° | OEt = 22.4 | 22.6 |
|  |  |  | Cl = 8.82 | 8.73 |
| IV | $C_{12}H_{21}O_6Br$ | b.p. 114°/0.5 torr | Br = 23.5 | 23.2 |
|  |  |  | OEt = 52.8 | 52.4 |
| V | $C_{11}H_{15}O_6NS$ | m.p. 158–160° | C = 45.7 | 45.8 |
|  |  |  | H = 5.19 | 5.24 |
|  |  |  | N = 4.84 | 4.93 |
|  |  |  | S = 11.1 | 11.2 |
|  |  |  | OEt = 31.1 | 30.6 |
| Diethyl acetoxymethylene malonate | $C_{10}H_{14}O_6$ | b.p. 109–110°/0.6 torr. | C = 52.2 | 52.1 |
|  |  |  | H = 6.08 | 6.30 |
| Diethyl oxomalonate, 2,4-dinitrophenylhydrazone | $C_{13}H_{14}N_4O_8$ | m.p. 115–117° | C = 44.1 | 44.9 |
|  |  |  | H = 3.95 | 4.36 |
|  |  |  | N = 15.8 | 15.6 |
|  |  |  | OEt = 25.4 | 24.8 |

I claim:

1. Diethyl 2-formyl-2 bromomalonate.

2. A method of preparing 2 halogen - 2 formyl malonic esters comprising suspending potassium oxymethylene diethyl malonate in carbon tetrachloride and halogenating the suspended ester at 0° C.

3. The method of claim 2 wherein bromine is the halogenating agent.

4. The method of claim 2 wherein chlorine is the halogenating agent.

5. A method of preparing l-2-(dicarbethoxymethylene)thiazolidine-4-carboxylic acid comprising reacting diethyl 2-formyl-2-bromomalonate with l-cysteine hydrochloride monohydrate, adding pyridine to precipitate out l-cystine treating the filtrate from the precipitation with saturated sodium bicarbonate, extracting the treated filtrate with chloroform and acidifying to obtain the thiazolidine.

* * * * *